United States Patent
Ishida

(10) Patent No.: US 10,398,014 B2
(45) Date of Patent: Aug. 27, 2019

(54) METHOD AND APPARATUS FOR RADIATING CHARGED PARTICLES, AND METHOD AND APPARATUS FOR EMITTING X-RAYS

(71) Applicant: BSR Co., Ltd., Aichi (JP)

(72) Inventor: Toshiyuki Ishida, Aichi (JP)

(73) Assignee: BSR CO., LTD., Aichi (JP)

( * ) Notice: Subject to any disclaimer, the term of this patent is extended or adjusted under 35 U.S.C. 154(b) by 202 days.

(21) Appl. No.: 15/516,836

(22) PCT Filed: Oct. 8, 2015

(86) PCT No.: PCT/JP2015/078691
§ 371 (c)(1),
(2) Date: Apr. 4, 2017

(87) PCT Pub. No.: WO2016/056639
PCT Pub. Date: Apr. 14, 2016

(65) Prior Publication Data
US 2017/0303379 A1    Oct. 19, 2017

(30) Foreign Application Priority Data

Oct. 8, 2014 (JP) .................................. 2014-207629

(51) Int. Cl.
*H05G 2/00* (2006.01)
*A61N 5/10* (2006.01)
(Continued)

(52) U.S. Cl.
CPC .................. *H05G 2/00* (2013.01); *A61B 6/40* (2013.01); *A61N 5/10* (2013.01); *H01J 35/065* (2013.01);
(Continued)

(58) Field of Classification Search
CPC .......... H05G 2/00; A61N 5/10; A61N 5/1077; A61N 2005/1019; A61N 2005/1022; A61B 6/00; A61B 6/40; G21K 5/00; G21K 5/04
(Continued)

(56) References Cited

FOREIGN PATENT DOCUMENTS

| WO | 2010116709 A1 | 10/2010 |
| WO | 2012005338 A2 | 1/2012 |

(Continued)

OTHER PUBLICATIONS

International Search Report and Written Opinion of the International Searching Authority dated Jan. 12, 2016 in parent case PCT/JP2015/078691.

(Continued)

*Primary Examiner* — Jurie Yun
(74) *Attorney, Agent, or Firm* — Polson Intellectual Property Law, PC; Margaret Polson

(57) ABSTRACT

In the present invention, a ferroelectric body is irradiated with ultraviolet light, and the ferroelectric body is caused to stably generate electric potential. A method for radiating charged particles, in which the UV-light-receiving surface of the ferroelectric body that receives UV light and is caused to generate a potential difference is irradiated with UV light having a wavelength not transmitted by the ferroelectric body, and charged particles are radiated from the charged-particle-radiation surface of the ferroelectric body, wherein the UV-light-receiving surface is irradiated with pulses of UV light at a peak power of 1 MW or greater. The pulse width of the UV light is measured in picoseconds (less than $1\times10^{-9}$ seconds), and the UV pulses can be transmitted by fiber.

13 Claims, 4 Drawing Sheets

(51) Int. Cl.
    *A61B 6/00*     (2006.01)
    *H01J 35/06*     (2006.01)

(52) U.S. Cl.
    CPC ............... *A61N 2005/1022* (2013.01); *A61N 2005/1088* (2013.01); *A61N 2005/1089* (2013.01); *A61N 2005/1091* (2013.01)

(58) Field of Classification Search
    USPC ................................. 378/64, 65, 119, 143
    See application file for complete search history.

(56) References Cited

FOREIGN PATENT DOCUMENTS

| | | | |
|---|---|---|---|
| WO | 2013035823 A1 * | 3/2013 | |
| WO | 2013058342 A1 | 4/2013 | |
| WO | 2014065284 A1 | 5/2014 | |

OTHER PUBLICATIONS

Kisa et al. Extended Abstracts (The 70th Autumn Meeting, 2009); The Japan Society of Applied Physics No. 2 10p-ZM-14.

* cited by examiner

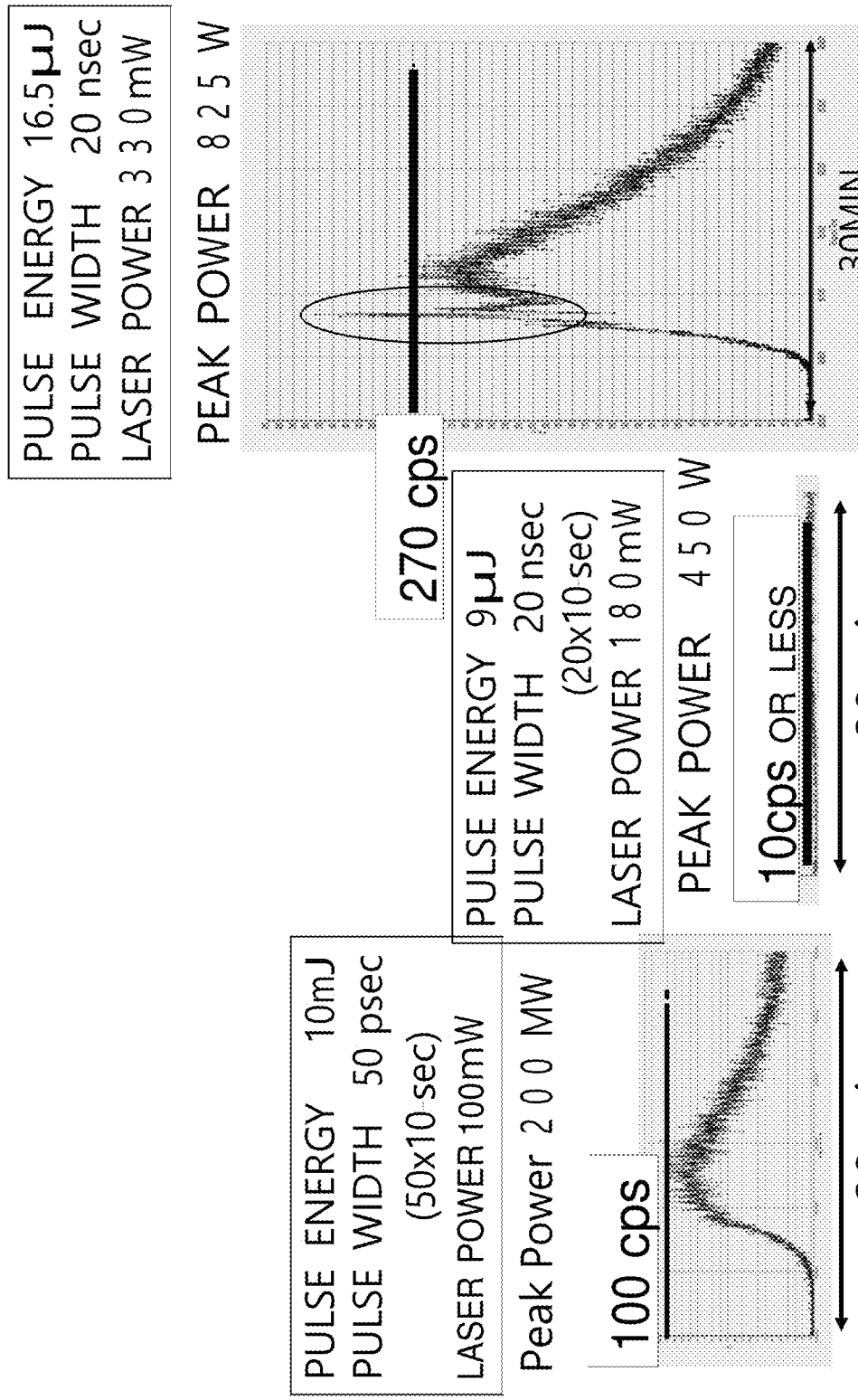

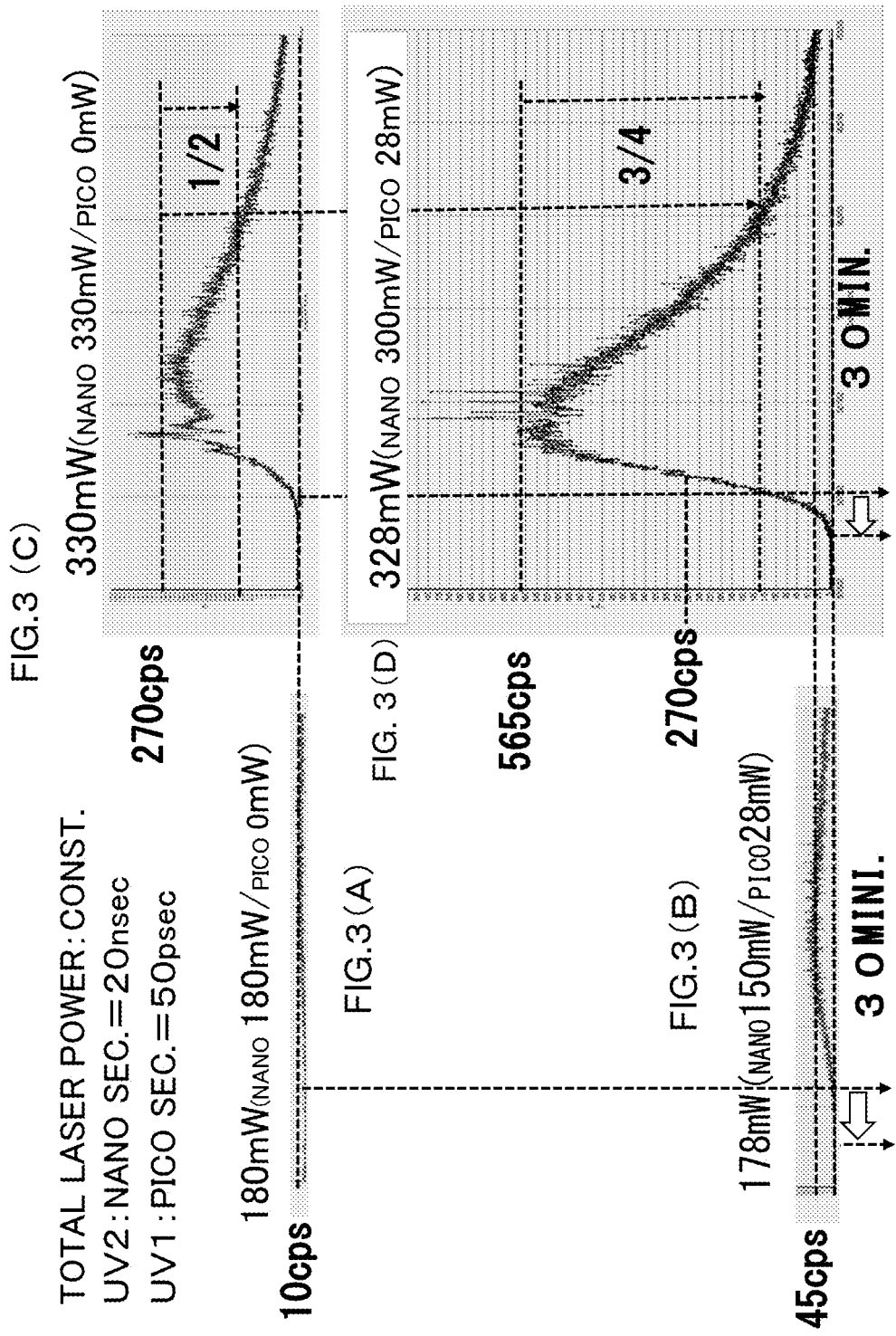

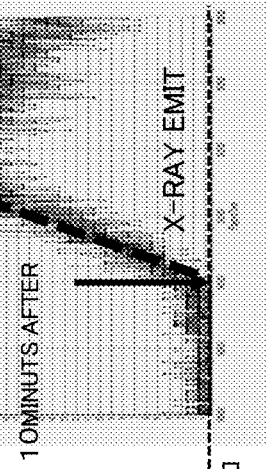
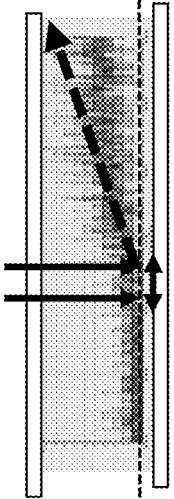
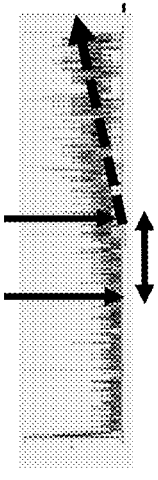
FIG.4 (A) PICO10mW/NANO150mW
FIG.4 (B) PICO20mW/NANO150mW
FIG.4 (C) PICO28mW/NANO150mW
CONDITION:
① NANO SEC. LASER POWER 150mW CONSTANT
② PREVIOUS IRRADIATION ONLY BY NANO SEC. LASER FOR 10 MINIUTS
③ IRRADIATION BY PICO SEC. LASER FOR 10 MINUTES

METHOD AND APPARATUS FOR RADIATING CHARGED PARTICLES, AND METHOD AND APPARATUS FOR EMITTING X-RAYS

TECHNICAL FIELD

The present invention relates to a charged particle emitting method and an apparatus therefor, and an X-ray generating method and an apparatus therefor.

BACKGROUND ART

The present inventor has found that charged particles such as electrons are emitted from a ferroelectric body when irradiated with controlled ultraviolet light to the ferroelectric body. And, as one application of the present invention, the inventor disclosed in Patent Document 1 showing a X-ray generator in which charged particles are emitted from the ferroelectric body to irradiate metal piece by irradiating the ferroelectric material with ultraviolet light.

PRIOR ART DOCUMENT

Patent Document

[Patent Document 1] WO 2010/116709 A1
[Patent Document 2] WO 2012/005338 A1
[Patent Document 3] WO 2013/035823 A1
[Patent Document 4] WO 2013/058342 A1
[Patent Document 5] WO 2014/065284 A1
[Non-Patent Document 1] Kisa et al. Extended Abstracts (The 70th Autumn Meeting, 2009); The Japan Society of Applied Physics No. 2 10p-ZM-14

SUMMARY OF THE INVENTION

Disclosure of the Invention

In the inventions described in Patent Documents 1 to 5, X-rays are not generated stably or evenly. An aspect of the present invention is to stabilize the emission of charged particles from the ferroelectric body on which the ultraviolet light are irradiated and also stabilize or even the emission of the X-ray.

SUMMARY OF THE INVENTION

The present inventor has made intensive studies to achieve the above object. As a result, the present invention has been conceived as follows. That is, one aspect of the present invention is defined as follows.

A charged particle emitting method for emitting charged particles from a charged particle emitting surface of a ferroelectric body which generates a potential difference due to irradiation on an ultraviolet receiving surface of the ferroelectric with an ultraviolet light having a wavelength incapable of passing through the ferroelectric body, wherein the ultraviolet light is pulsed light and has a peak power of the pulsed light is 1 MW or more.

According to the charged particle emitting method defined as above, when irradiating a pulsed light with strong peak power of 1 MW or more, charged particles are emitted from the charged particle emitting surface in response to the irradiation. Charged particles thus emitted are irradiated on a metal piece so that an X-rays are emitted from the metal piece.

It is known that when a ferroelectric body is irradiated with ultraviolet light, a potential difference is generated between the ultraviolet light receiving surface and the opposite surface (charged particle emitting surface). At this time, since the charged particle emitting surface is charged negative, a repulsive force is applied to the electrons present on the charged particle emitting surface.

According to the research by the present inventor, it was impossible to emit electrons stably from the charged particle emitting surface merely by charging negative. In other words, the emission of electrons could not be controlled.

For example, as shown in Patent Document 5, when a ferroelectric body is irradiated with an ultraviolet light laser (continuous light), a stable potential difference is generated between the ultraviolet light receiving surface and the charged particle emitting surface. However, the emission of electrons from the charged particle emitting surface were not observed and hence no X-ray emission.

The present inventor noticed that the difference between the above and the case where the generation of X-rays was successful in Patent Document 1 and the like is the change or shift on the potential of the charged particle emitting surface of the ferroelectric body.

That is, in the latter case, it was noticed that the potential of the charged particle emitting surface of the ferroelectric body gradually changed.

Then, as a measure to change the potential of the charged particle emitting surface, when irradiated with ultraviolet light pulses with high peak power, electrons are emitted in response to the irradiation of the ultraviolet light pulses, so that X-rays were emitted in response to the irradiation with ultraviolet light pulses. That is, by irradiating the ultraviolet light receiving surface with pulsed ultraviolet light having a peak power of 1 M (mega) W or more, generation of X-rays can be controlled.

Even if ultraviolet light pulses with a peak power less than 1 MW are irradiated onto the ultraviolet light receiving surface, charged particles are not emitted from the charged particle emitting surface of the ferroelectric body or hardly stabilized even if they are emitted.

The peak power may be 50 MW or more. The peak power may be 100 MW or more.

The reason, why charged particles are emitted from the charged particle emitting surface to cause the generation of X rays by irradiating the ultraviolet light receiving surface with ultraviolet light pulses with a peak power of 1 MW or more, is currently studied. The inventor thinks of that irradiation of the ultraviolet light of such a strong peak power causes a change (or vibration) in potential on the charged particle emitting surface. As a result, it is predicted that electrons are easily separated from the charged particle emitting surface. Also, it seems that the photoacoustic effect is also influenced.

Although it depends on future study, the inventor also expects the following hypothesis. When ultraviolet light having a wavelength that does not pass through the ferroelectric body is irradiated on the surface (ultraviolet light receiving surface) where negative end of the electric dipole of the ferroelectric body appears, electrons in the ferroelectric body are excited. The influence of the excited electrons propagates to the surface (charged particle emitting surface) where the positive end of the electric dipole of the ferroelectric body appears and lowers its potential. Here, in order to separate a sufficient amount of electrons from the charged particle emitting surface to generate X-rays, some stimulation is required on the surface, and as a stimulus thereof, a peak power of 1 M (Mega) W or more is irradiated on the surface of the body. When such ultraviolet light with a high peak power is irradiated to the ultraviolet light receiving surface of the ferroelectric body in a pulsed manner, the electric potential violently vibrates on the charged particle emitting surface and the photoacoustic effect also acts, so that the charged particles adsorbed on the charged particle emitting surface are desorbed.

The desorbed electrons are urged in a direction away from the charged particle emitting surface by an electric field generated by the surface.

Note that the electrons in the ferroelectric body excited by ultraviolet light also affect lattice vibration of the ferroelectric body and may raise the temperature of the ferroelectric body. Due to this temperature rise, a so-called pyroelectric effect occurs and the potential of the charged particle emitting surface of the ferroelectric body may change. Even if the temperature change does not occur, when ultraviolet light having a wavelength that does not pass through the ferroelectric body is irradiated onto the ultraviolet light receiving surface, a potential difference is generated between the both surfaces of the ferroelectric body.

BRIEF DESCRIPTION OF THE DRAWINGS

FIGS. 2(A) through 2(C) depict charts showing a comparison of emitted X-ray emission amounts with respect to a difference in peak power of ultraviolet light pulses.

FIGS. 3(A) through 3(D) depict charts showing a comparison of X-ray emission amounts when irradiation with ultraviolet light pulses of low peak power only and ultraviolet light pulses with high peak power as well as low peak power are irradiated thereon;

FIGS. 4(A) through 4(C) depict graphs showing the relationship between the X-ray emission amount when the peak power of the high peak power ultraviolet light pulses is changed as well as irradiating low peak power ultraviolet light pulses.

DETAILED DESCRIPTION OF THE INVENTION

Figure 1:
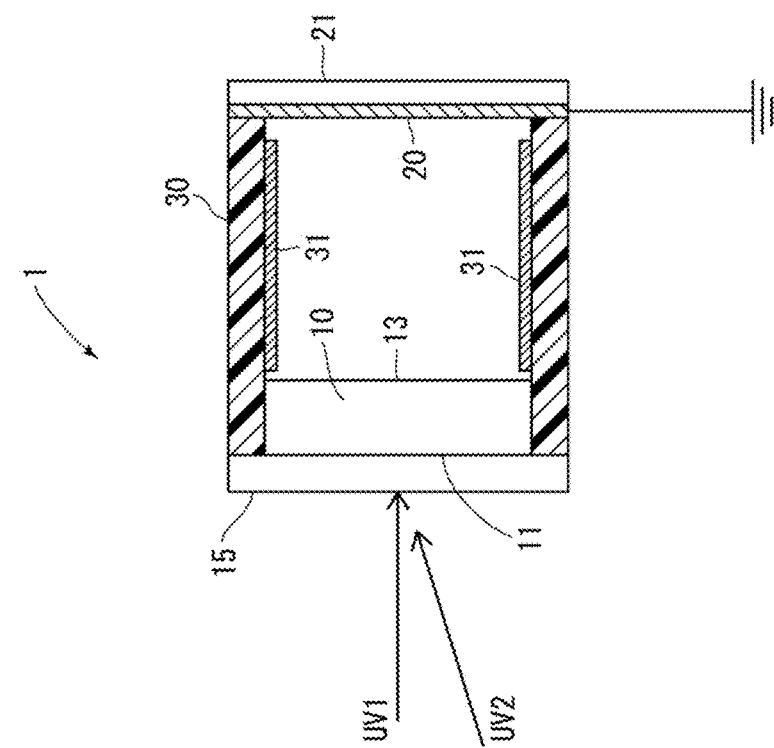
FIG. 1 is a cross-sectional view schematically showing a configuration of an X-ray emitting apparatus according to an embodiment of the present invention.

Hereinafter, a plurality of embodiments of the present invention will be described.

FIG. 1 schematically shows the configuration of the X-ray emission apparatus 1 according to the embodiment.

The X-ray emission apparatus 1 includes a ferroelectric body 10, a copper foil 20, and a casing 30.

As the ferroelectric body 10, a pyroelectric such as $LiNbO_3$ or $LiTaO_3$ can be used. For example, in the crystal body of $LiNbO_3$, since the center of gravity of the positive charge ($Li^+$, $Nb^{5+}$) and the center of gravity of the negative charge ($O^{2-}$) do not coincide with each other, even in a steady state, polarization is occurring. Charge particles of electrically equivalence and opposite polarization are absorbed on the surface to keep the body be neutralized.

In the ferroelectric body 10, the electric dipoles are aligned on one side, the negative side is the ultraviolet light receiving surface 11, and the positive side thereof is the charged particle emitting surface 13.

The shape of the ferroelectric body 10 can be arbitrarily determined according to the housing 30 as long as the negative end surface (that is, the ultraviolet light receiving surface) and the positive end side surface (that is, the charged particle emitting surface) of the electric dipole are obtained. The distance between the ultraviolet light receiving surface 11 and the charged particle emitting surface 13 can also be arbitrarily designed according to the target potential difference of the ferroelectric body 10.

It is preferable to adhere the ultraviolet light receiving surface 11 to the dielectric support plate 15 such as quartz glass which transmits the ultraviolet light. The support plate 15 also has the function of blocking external heat influence on the ferroelectric 10, and for this purpose, the thickness of the support plate 15 is preferably 1.0 mm or more.

The upper limit of the thickness is not particularly limited, but it can be arbitrarily selected within a range not affecting the transmission of ultraviolet light pulses. The supporting plate 15 also has the function of releasing the heat accumulated in the ferroelectric 10 to the outside.

The copper foil 20 is irradiated with charged particles to emit X-rays. Any metal piece capable of emitting X rays can be substituted for the copper foil 20. It is preferable to support the surface of the copper foil 20 with a protective sheet 21 (for example, a polyimide sheet) which transmits X-rays and can maintain vacuum.

The copper foil 20 is grounded.

It can be seen that if the copper foil 20 is regarded as an extraction electrode, the apparatus of FIG. 1 is regarded as a charged particle emitting apparatus.

For the housing 30, a pipe made of polypropylene was adopted. Of course, any material such as other resin material, metal material, ceramic material or the like can be used as the material of the housing 30 as long as it can maintain the vacuum.

When an insulating material, particularly a resin material is selected, in order to prevent the inner circumferential surface from being charged up by the charged particles emitted from the charged particle emitting surface 13, it is preferable to provide protective layer 31 made of a conductive material.

When the housing 30 is made of a conductive material such as metal and the ferroelectric body 10 is inserted into the housing 30, in order to prevent the ultraviolet light receiving surface 11 and the charged particle emitting surface 13 from being short-circuited, an insulating layer is interposed between the housing 30 and the ferroelectric body 10. Also, it insulates the housing 30 from the copper foil 20.

The housing 30 covers at least the charged particle emitting surface 13 of the ferroelectric body 10 so that it is exposed to a vacuum space. In this case, since other portions of the ferroelectric body 10, that is, the peripheral surface and the ultraviolet light receiving surface 11 (including the case where the supporting plate 15 is provided) may be present in the atmosphere. This configuration improves the cooling effect of the ferroelectric body 10 in comparison with a configuration of an entire ferroelectric body 10 is in vacuum area.

One end of the housing 30 is covered with the support plate 15 and the other end is covered with the copper foil 20, so that the internal space of the casing 30 is airtightly shielded from the outside. In order to evacuate the inside of the housing 30, in the embodiment, a through hole (not shown) is formed in the housing 30 to evacuate with a vacuum pump.

It is preferable to introduce a reducing gas such as isobutyl alcohol into the internal space of the housing 30. This is for replenishing the charged particles emitted from the charged particle emitting surface.

Electrons are emitted exclusively from the charged particle emitting surface of the ferroelectric body, but also negative ions adsorbed on the charged particle emitting surface or existing on the surface thereof are also emitted.

Ultraviolet light having a wavelength that does not pass through the ferroelectric body 10 is irradiated to the ultraviolet light receiving surface 11 of the ferroelectric body 10 via the support plate 15.

In the present invention, pulsed ultraviolet light UV1 having a peak power of 1 MW or more is irradiated.

If the pulse width of the pulsed ultraviolet light UV1 is set to less than $1 \times 10^{-9}$ seconds, so-called picoseconds, even if the peak power is large, the energy per pulse becomes small, so that the pulsed ultraviolet light can pass through a usual ultraviolet light fiber In the example of FIG. 1, ultraviolet light UV2 and the ultraviolet light UV1 are irradiated simultaneously. Ultraviolet light UV2 is pulsed ultraviolet light or continuous light having a peak power of 100 kW or less. By irradiating the ultraviolet light UV2, the potential of the charged particle emitting surface of the ferroelectric body 10 decreases. However, with this ultraviolet light UV2 only, charged particles having high energy to generate X rays are not released or emitted.

Both ultraviolet light UV1 and ultraviolet light UV2 are preferably irradiated perpendicularly to the ultraviolet light receiving surface 11. When irradiating ultraviolet light UV1 and ultraviolet light UV2 to the same point on the ultraviolet light receiving surface 11, it is preferable to irradiate the pulsed ultraviolet light UV1 having a peak power of 1 MW or more substantially perpendicularly to the ultraviolet light irradiation surface.

When irradiated with ultraviolet light, the potential difference occurring on both sides of the ferroelectric (the ultraviolet light receiving surface and the charged particle emitting surface, the same shall apply hereinafter) depends on the material and thickness of the ferroelectric body (the distance between the ultraviolet light receiving surface and the charged particle emitting surface, The same applies hereinafter) are equal, it is considered to depend on the power (W/time) of the irradiated ultraviolet light.

If the power of the irradiated ultraviolet light is sufficiently high, it is expected that the ferroelectric body is heated and charged particles may be emitted from the charged particle emitting surface due to so-called pyroelectric effect.

Hereinafter, embodiments of the present invention will be described.

In the X-ray apparatus shown in FIG. 1, discotic $LiTaO_3$ having a diameter of about 10 mm and a width of about 6 mm was used as the ferroelectric body 10 and the ultraviolet light receiving surface 11 was adhered to the surface of a synthetic quartz plate 15 having a thickness of 1 mm by a high vacuum u agent (trade name: Torrseal).

A polypropylene pipe having an inner diameter of about 12 mm was used as the housing 30, and a protective film 31 made of a conductive coating material was formed on the inner peripheral surface thereof by coating. The thickness of the copper foil 20 was about 10 μm, and a polyimide protective sheet 21 was attached to the surface. The copper foil 20 is grounded and fixed to the housing 30 while maintaining insulation thereto.

The distance between the charged particle emitting surface 13 of the ferroelectric body 10 and the copper foil 20 was 4.5 mm, and the inside of the housing 30 was depressurized to $4 \times 10^{-1}$ Pa by a vacuum pump.

Ultraviolet light having a wavelength of 266 nm was irradiated to the ferroelectric body 10 of the X-ray emitting apparatus 1 with pulses having a pulse energy of 10 mJ and a pulse width of 50 psec. The laser power is 100 mW, and the peak power of each pulse is 200 MW. The results are shown in FIG. 2(A).

Similarly, FIG. 2(B) shows the result of irradiating the ferroelectric body 10 with ultraviolet light having a wavelength of 266 nm with a pulse energy of 9 μJ and a pulse width of 20 psec. The laser power is 180 mW, and the peak power of the pulse is 450 W. Compared with FIG. 2(A), since a larger laser power is input in FIG. 2(B), a larger potential difference is generated in the ferroelectric body 10. However, in the condition of FIG. 2(B), since the peak power is insufficient, emission of X-rays is hardly observed.

FIG. 2(C) shows the result of irradiating the ferroelectric body 10 with ultraviolet light having a wavelength of 266 nm with a pulse energy of 16.5 μJ and a pulse width of 20 psec. The laser power is 330 mW, and the peak power of the pulse is 825 W.

As shown in FIG. 2(C), when the laser power becomes strong, it is considered that so-called pyroelectric effect occurs and X-rays are generated.

In the X-ray emitting apparatus shown in FIG. 1, an ultraviolet light pulse having a pulse width of 50 psec was used as the ultraviolet light UV1, an ultraviolet light pulse having a pulse width of 20 psec was used as the ultraviolet light UV2, and the generated amount (dose) of X rays and intensity of irradiated ultraviolet light are shown in FIG. 3.

In the example of FIG. 3(A) and FIG. 3(B), total laser power were weak, that is 180 mW and 179 mW respectively. X-rays were generated only in example FIG(B) in which strong peak power ultraviolet light UV1 was irradiated, that is, the ultraviolet light UV1 (pico 28 mW) has about 50 MW peak power and the ultraviolet light UV2 (nano 180 W) has 1 kW or less.

FIG. 3(C) and FIG. 3(D) show the influence of the presence or absence of ultraviolet light UV1 when the power of ultraviolet light UV2 is increased to increase the total laser power. From these results, it can be seen that by irradiating a picosecond laser having a large peak power, the amount of generated X-rays is markedly increased. Note that the peak power of ultraviolet light UV2 (nano 330 mW, 300 mW) is less than 1 kW.

From the comparison between FIG. 3(B) and FIG. 3(D), it is found that the amount of generated X-rays increases when the total laser power is increased. This is thought to be due to the fact that when the total laser power is increased, the potential difference generated between both surfaces of the ferroelectric body increases.

This shows that charged particles can be efficiently detached from the charged particle emitting surface of the ferroelectric body by preliminarily generating a potential difference between both surfaces of the ferroelectric body (referred to as auxiliary boosting).

In the example of FIG. 3, ultraviolet light pulses with a low peak power are used during auxiliary boosting, but continuous light of ultraviolet light of a wavelength that does not pass through the ferroelectric can be used. In addition, a potential difference may be generated between both surfaces of the ferroelectric body by utilizing the pyroelectric effect by heating. During auxiliary boosting, it is preferable to control the laser power and heating amount so that charged particles do not separate from the charged particle emitting surface of the ferroelectric body.

FIG. 4 shows the emission of X-rays when a high peak power ultraviolet light pulses are irradiated at the same timing (10 minutes after the start of auxiliary boosting) on ferroelectric body.

The peak power in FIG. 4(A) is 20 MW, the peak power in FIG. 4(B) is 40 MW, and the peak power in FIG. 4(C) is 56 MW.

From the results shown in FIG. 4, it can be seen that as the peak power of the ultraviolet light pulse to be irradiated increases, the charged particles are efficiently detached from the charged particle emitting surface of the ferroelectric body.

The present invention is not limited to the description of the embodiments and examples of the invention at all. Various modifications are also included in the present invention as long as they can be easily conceived by those skilled in the art without departing from the description of the scope of claims.

The characteristic configurations of the above embodiments and each example may be combined within a feasible range.

The X-rays generated by the X-ray generating apparatus of the present invention can be used for treatment of the human body. For example, cancer of the esophagus, stomach cancer, colon cancer, liver cancer, gall bladder cancer, pancreatic cancer, breast cancer, laryngeal cancer, head and neck cancer, ovarian cancer, cervical cancer, endometrial cancer, It can be used as radiotherapy for renal cell carcinoma, bladder cancer, prostate cancer, testicular tumor, lung cancer, mediastinal tumor, bone-soft tumor, skin cancer, malignant melanoma, brain tumor, leukemia, malignant lymphoma etc.

Further, since the X-ray generating apparatus and the charged particle emitting apparatus of the present invention can be made thinner, they can be incorporated in a catheter or an endoscope.

The X-ray generating apparatus of the present invention has uniform X-ray wavelengths and has a small radiation angle, so it can be suitably used for surface treatment of fine materials. The electron beam generator of the present invention is also applicable to the surface treatment of materials.

The X-ray generator of the present invention can be used as an X-ray source of a nondestructive inspection apparatus or a medical observation apparatus.

The invention claimed is:

1. A method for emitting charged particles from a ferroelectric body which has an ultraviolet light receiving surface and a charged particle emitting surface, comprising:
    a step for auxiliary booting to preliminarily generate a potential difference between the ultraviolet light receiving surface and the charged particle emitting surface, and
    a step for irradiating onto the ultraviolet light receiving surface of the ferroelectric body with an ultraviolet light having a wavelength incapable of passing through the ferroelectric body, wherein the ultraviolet light is pulsed light and has a peak power of 1 MW or more, and by which the charged particles stably emitting from the charged particle emitting surface.

2. The method according to claim 1, wherein the pulsed ultraviolet light has a pulse width of less than $1 \times 10^{-9}$ seconds.

3. The method according to claim 2, wherein the pulsed ultraviolet light is irradiated onto the ultraviolet light receiving surface of the ferroelectric body via a fiber.

4. The method according to claim 1, wherein a pulsed ultraviolet light having a peak power of 100 kW or less is irradiated onto the ultraviolet light receiving surface of the ferroelectric body to preliminarily generate the potential difference between the ultraviolet light receiving surface and the charged particle emitting surface of the ferroelectric body.

5. The method according to claim 1, the auxiliary booting is performed by irradiating a continuous ultraviolet light onto the ultraviolet light receiving surface of the ferroelectric body.

6. The method according to claim 1, the auxiliary booting is performed by heating the ferroelectric body so as not to radiate the charged particles from the charged particle emitting surface.

7. A method for emitting X-rays, comprising irradiating a metal piece with charged particles emitted by the charged particle emitting method according to claim 1, and emitting X rays from the metal piece.

8. An X-ray emitting apparatus, comprising:
    a ferroelectric body having an ultraviolet light receiving surface and a charged particle emitting surface,
    a light source for irradiating the ultraviolet light receiving surface of the ferroelectric body with ultraviolet light having a wavelength which does not pass through the ferroelectric body by which a potential difference is generated between the both surfaces of the ferroelectric body, and
    a metal piece disposed opposite the charged particle emitting surface of the ferroelectric body, the metal piece emitting X-rays by receiving charged particles emitted from the charged particle emitting surface-,
    wherein the light source irradiates the ultraviolet light receiving surface with pulsed ultraviolet light having a peak power of 1 MW or more, and
    wherein further comprising an auxiliary booster that preliminarily generates a potential difference between the ultraviolet light receiving surface and the charged particle emitting surface of the ferroelectric body before irradiating by the ultraviolet light.

9. The X-ray emitting apparatus according to claim 8, wherein a pulse width of the pulsed ultraviolet light is less than $1 \times 10^{-9}$ seconds.

10. The X-ray emitting apparatus according to claim 8, wherein the auxiliary booster is a heater.

11. A charged particle emitting apparatus, comprising:
    a ferroelectric body having an ultraviolet light receiving surface and a charged particle emitting surface,
    a light source for irradiating the ultraviolet light receiving surface of the ferroelectric body with ultraviolet light having a wavelength which does not pass through the ferroelectric body by which a potential difference is generated between the both surfaces of the ferroelectric body, and
    an electrode disposed opposite the charged particle emitting surface of the ferroelectric body,
    wherein the light source irradiates the ultraviolet light receiving surface with pulsed ultraviolet light having a peak power of 1 MW or more, and
    wherein further comprising an auxiliary booster that preliminarily generates a potential difference between the ultraviolet light receiving surface and the charged particle emitting surface of the ferroelectric body before irradiating by the ultraviolet light.

12. The charged particle emitting apparatus according to claim 11, wherein the pulsed ultraviolet light has a pulse width of less than $1 \times 10^{-9}$ seconds.

13. The charged particle emitting apparatus according to claim 11, wherein the auxiliary booster is a heater.

* * * * *